United States Patent
Wieder et al.

(10) Patent No.: US 6,242,268 B1
(45) Date of Patent: *Jun. 5, 2001

(54) HOMOGENEOUS FLUORASSAY METHODS EMPLOYING FLUORESCENT BACKGROUND REJECTION AND WATER-SOLUBLE RARE EARTH METAL CHELATES

(75) Inventors: Irwin Wieder, Los Altos; Ron L. Hale, Woodside, both of CA (US)

(73) Assignee: EG&G Wallac, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/184,330

(22) Filed: Nov. 2, 1998

Related U.S. Application Data

(63) Continuation of application No. 08/732,871, filed on Oct. 15, 1996, now Pat. No. 5,830,769, which is a continuation of application No. 08/338,285, filed on Nov. 10, 1994, now abandoned, which is a continuation of application No. 08/035,516, filed on Mar. 22, 1993, now abandoned, which is a continuation of application No. 06/875,287, filed on Jun. 17, 1986, now abandoned, which is a continuation-in-part of application No. 06/712,774, filed on Mar. 18, 1985, now Pat. No. 4,761,481.

(51) Int. Cl.[7] .................... G01N 33/536; C03B 37/075; E21B 47/00; H01B 1/06; H01J 31/50

(52) U.S. Cl. .............. 436/538; 65/390; 175/41; 252/521.1; 264/21; 313/526; 378/44

(58) Field of Search ................. 615/390; 175/41; 252/521.1; 264/21; 313/526; 378/44; 424/1.53, 9.6; 426/240; 436/82, 84, 172, 546; 536/25.32; 600/317, 321

(56) References Cited

U.S. PATENT DOCUMENTS

| | | | |
|---|---|---|---|
| 3,901,654 | 8/1975 | Gross | 23/230 B |
| 3,939,350 | 2/1976 | Kronick et al. | 250/365 |
| 3,998,943 | 12/1976 | Ullman | 424/12 |
| 4,020,151 | 4/1977 | Bolz et al. | 424/1.5 |
| 4,058,732 | 11/1977 | Wieder | 250/461 B |
| 4,220,450 | 9/1980 | Maggio | 23/230 B |
| 4,283,382 | 8/1981 | Frank et al. | 424/8 |
| 4,341,957 | 7/1982 | Wieder | 250/461.2 |
| 4,352,751 | 10/1982 | Wieder et al. | 260/112 R |
| 4,374,120 | 2/1983 | Soini et al. | 436/546 |
| 4,761,481 | 8/1988 | Hale et al. | 546/296 |
| 4,925,804 | 5/1990 | Hale et al. | 546/296 |
| 5,830,769 | * 11/1998 | Weider et al. | 436/436 |

FOREIGN PATENT DOCUMENTS

| | | |
|---|---|---|
| 0064484 | 4/1982 | (EP) . |
| 0068875 | 6/1982 | (EP) . |
| 0103558 | 9/1983 | (EP) . |

OTHER PUBLICATIONS

Thomas et al., "Fluorescence Energy Transfer in the Rapid–Diffusion Limit," Proc. Nat'l. Acad. Sci., USA, 75(12):5746–5750 (Dec. 1978).
J. Biol. Chem. 251 4172–8 (1976).
Clin. Chem. Winston Salem, NC 29(1) 65–8 (1983).
Proc. Nat'l. Meet. Biophys. Med. Eng. Finl. 4 199–202 (1982).
"A Review of Fluorimmunoassay and Immunofluorometric Assay" D.S. Smith et al., Ann. Clin. Biochem. 18 (1981) 253–274.
Shaw et al., J. Clin. Pathol., 1977, 30, 526–31.
Broughton et al., Clin. Chem., 1978, 24, 1033.
Shaw et al., Clin. Chem. 1979, 25, 322–5.
Danliker et al., Immunochemistry, 1979, 7, 799–828.
Nargessi et al., J. Immunol. Meth, 1979, 26, 307–313.
Lopatin et al., Biochemistry 1971, 10, 208–13.
Portmann et al., Immunochemistry 1975, 12, 461–6.
Levison et al., Biochemisty 1970, 9, 322–31.
Voss et al., Immunochemistry 1976, 13, 447–53.
Nargessi et al., Clin. Chem. Acta. 1978, 89, 461–7.
Zuk et al., Clin. Chem., 1979, 25, 1554–60.
Brinkley et al., Clin. Chem., 1979, 25, 1077.
D.S. Smith, FEBS Lett. 77, 25–7 (1977).

* cited by examiner

Primary Examiner—Lynette R. F. Smith
Assistant Examiner—Ja-Na A. Hines
(74) Attorney, Agent, or Firm—Finnegan, Henderson, Farabow, Garrett & Dunner, L.L.P.

(57) ABSTRACT

Homogeneous assays for determining quantitatively the extent of a specific binding reaction can be carried out effectively on very dilute solutions using measurements of fluorescence if a fluorescence measurement scheme that is capable of rejecting short-lived background fluorescence is employed and if the fluorescent group being measured has the following properties: a. the group being measured must be a rare earth metal chelate complex combination; b. the chelate must be water-soluble; c. the complex combination must also be stable in extremely dilute aqueous solutions, that is, the measured chelate must have at least one ligand having a metal-to-ligand binding constant of at least about $10^{13}M^{-1}$ or greater and it must have a fluorescent emission that is long-lived compared to the longest decay lifetime of ambient substances and have a half life of from 0.01 to 50 msec.

20 Claims, 1 Drawing Sheet

HOMOGENEOUS FLUORASSAY METHODS EMPLOYING FLUORESCENT BACKGROUND REJECTION AND WATER-SOLUBLE RARE EARTH METAL CHELATES

This application is a continuation of U.S. Ser. No. 08/732,871, filed Oct. 15, 1996, now U.S. Pat. No. 5,830,769, which is a continuation of U.S. Ser. No. 08/338,285, filed Nov. 10, 1994, now abandoned, which is a continuation of U.S. Ser. No. 06/875,287, filed Jun. 17, 1986, now abandoned, which is a continuation-in-part of U.S. Ser. No. 06/712,774, filed Mar. 18, 1985, now U.S. Pat. No. 4,761,481 and also a Cont. of U.S. Ser. No. 08/035,516, now abandoned.

BACKGROUND OF THE INVENTION

1. Field of the Invention

This invention relates to specific binding fluoroassay assay techniques. More particularly, it relates to homogeneous specific binding fluorassay techniques which employ water-soluble rare earth metal chelate fluorophores together with fluorescence measurements which eliminate or reject interferring background fluorescence and permit direct and highly sensitive determination of analytes in aqueous media.

Specific binding assay techniques are useful for determining various substances of diagnostic, medical, environmental and industrial importance which appear in liquid media at very low concentrations. Specific binding assays are based on a specific interaction between the analyte under determination and a binding partner therefor. Where one of the analyte and its binding partner is an antibody and the other is a corresponding hapten or antigen, the assay is known as an immunoassay.

In such assays, it is necessary to have a tag or label present which can give a measurable indication of the extent to which the specific binding reaction takes place. For example, fluorescent labels can be present on the binding partner and the incorporation of this fluorescent label into the specifically bound pair can be used to detect formation of the pair. Alternatively, the specific binding reaction can give rise to a change in the fluorescence properties of the fluorophore. As outlined by I. Wieder in U.S. Pat. No. 4,058,732, the detection of this fluorescence can be made more sensitive by employing time-gated detection to reject short-lived background fluorescence and more accurately detect long-lived fluorescence such as emitted by rare earth metal chelates. These background rejection techniques have been employed with advantage heretofore in a variety of heterogeneous analysis methods. A heterogeneous assay is one in which the fluorescently labeled pair is physically separated from unbound fluorophores.

The present invention provides techniques in which the background rejection methods are applied to homogeneous assays. A homogeneous assay is one in which the fluorescently labeled pairs are not separated from the unbound fluorophores but the bound fluorophores and unbound fluorophores are distinguishable from one another. See J. BIOL. CHEM., 251, 4172–8 (1976).

2. Description of the Prior Art

U.S. Pat. No. 4,058,732, issued on Nov. 15, 1977 to Irwin Wieder describes the use of fluorescent background rejection in assay techniques.

U.S. Pat. No. 4,341,957, issued to Irwin Wieder describes antibodies coupled to fluorescent rare earth chelates.

U.S. Pat. No. 4,352,751 issued on Oct. 5, 1982 to Wieder and Wollenberg discloses a family of rare earth metal chelates and their use in fluorescent background rejection techniques. Similarly, European Patent Application 68875 A2 filed on Jun. 28, 1982 of Eastman Kodak Co. discloses fluorescent rare earth chelate labels in fluoroassay techniques.

European Patent Application 64484 A2 of Wallac Oy discloses a heterogeneous assay method wherein a lanthanide chelate is coupled to a specific binding substance, reacted in a binding reaction and isolated from the binding reaction reaction mixture by physical separation. The lanthanide ion label is then released from the chelate by an acid treatment and measured using the Wieder fluorescence background rejection technique. Other references of interest include articles appearing at CLIN. CHEM., Winston Salem, N.C., 29(1) 65–8 (1983) and PROC. NATL. MEET. BIOPHYS. MED. ENG. FINL., 4, 199–202 (1982) and U.S. Pat. No. 4,374,120 all from the Wallac Oy group: and Kodak's U.S. Pat. No. 4,283,382, issued Aug. 11, 1981.

A recent item of interest is European Patent Application 103558 published Mar. 21, 1984 in which the Wallac Oy group proposed the use of fluorescence background rejection in certain homogeneous assay settings. However, the method shown in that patent application utilizes reagents that are normally insoluble and weakly fluorescent in water and employs complicated micelle formation techniques to enable the use of these reagents with aqueous test media. This inability to operate directly in aqueous media is a serious failing since virtually every important specific binding reaction is identified primarily in aqueous systems.

Other art to be noted, but probably less in point, includes the article "A Review of Fluoroimmunoassay and Immunofluorometric Assay", D. S. Smith et al, ANN. CLIN. BIOCHEM., 18, (1981) 253–274 which provides a summary of the heterogeneous and homogeneous fluoroassay techniques proposed heretofore; U.S. Pat. Nos. 3,998,943; 4,020,151; 3,939,350; 4,220,450 and 3,901,654 which show analytical assay techniques.

There are two general types of homogeneous fluoroassays. In the more common of these, the bound fluorophores have a decreased or "quenched" fluorescence as compared to the unbound fluorophores so that the extent of binding can be detected by a decrease in fluorescence. A variety of quenching assays have been proposed. (See, for example, Shaw, et al, J. CLIN. PATHOL. 1977, 30, 526–31; Broughton, et al, CLIN. CHEM. 1978, 24, 1033; Shaw, et al, CLIN. CHEM. 1979, 25, 322–5; Dandliker, et al, IMMUNOCHEMISTRY 1970, 7, 799–828; Nargessi, et al, J. IMMUNOL. METH. 1979, 26, 307–313; Lopatin, et al, BIOCHEMISTRY 1971, 10, 208–13; Portmann, et al, IMMUNOCHEMISTRY 1975, 12, 461–6; Levison, et al, BIOCHEMISTRY 1970, 9, 322–31; Voss, et al, IMMUNOCHEMISTRY 1976, 13, 447–53; Nargessi, et al, CLIN CHEM ACTA 1978, 89, 461–7; Zuk, et al, CLIN CHEM 1979, 25, 1554–60 and Brinkley, et al, CLIN CHEM 1979, 25, 1077.) Similarly, SYVA corporation has proposed a fluorescein-rhodamine homogeneous assay system in which the fluorescein is affixed to the antigen and the rhodamine is affixed to the antibody. When these two groups are brought together, quenching results.

In the other type of homogeneous fluoroassay, the bound fluorophore has an increased or "enhanced" fluorescence as compared to the unbound fluorophore. See D. S. Smith, FEBS LETT., 77, 25–7, (1977) in which a fluorescein-labeled $T_4$ was used to accomplish an enhancement.

The foregoing techniques have been based in general upon the use of rhodamines and fluorescein, for the most part, and have not been based upon materials such as the rare earth chelates which are particularly advantageous in the setting of fluorescence background rejection. Notwithstanding the recognized advantages of homogeneous assays and of fluorescence background rejection as analysis techniques there has not yet been provided the methodology to merge these two technical advances in a general practical way so as to effectively analyze the wide range of extremely dilute aqueous solutions which the field provides. More particularly, there has been no effective application of these techniques to provide an enhancement fluorescence assay. This failure is especially important because a main field of interest involves samples which have concentrations of analyte less than $10^{-8}$ molar, especially in the $10^{-8}$ to $10^{-14}$ molar range and below, which is pertinent to determining natural products, hormones, serum proteins, and the like. It is the primary object of this invention to provide practical homogeneous assays for analytes in dilute aqueous media using fluorescence background rejection as the detection event.

STATEMENT OF THE INVENTION

It has now been found that homogeneous assays for determining quantitatively the extent of a specific binding reaction can be carried out effectively on very dilute solutions using measurements of fluorescence if a fluorescence measurement scheme that is capable of rejecting short-lived background fluorescence is employed and if the fluorescent group being measured has the following properties: a. the group being measured must be a rare earth metal chelate complex combination; b. the chelate must be water-soluble; c. the complex combination must also be stable in extremely dilute aqueous solutions, that is, the measured chelate must have at least one ligand having a metal-to-ligand binding constant of at least about, $10^{13}M^{-1}$ or greater and it must have a fluorescent emission that is long-lived compared to the longest decay lifetime of ambient substances and have a half life of from 0.01 to 50 msec. The use of such a measurement regimen and such a fluorescent material makes possible a method of analysis of this invention which comprises (a) admixing a first tag-containing biospecific group-containing compound with its biospecific counterpart thereby forming a specific binding pair which, as a result of said specific binding, contains a new tag which is different in fluorescence as compared to said first tag, at least one of said first tag and said new tag being a fluorescent chelate comprising a rare earth metal in complex combination with ligand, said chelate being water-soluble and water-stable and having a ligand-to-metal binding constant of at least about $10^{13}M^{-1}$, and a decay lifetime which is long compared to the longest decay lifetime of ambient substances (i.e., a half life in the 0.01 to 50 msec range); (b) exciting the aqueous liquid product of step (a) with at least one pulse of electromagnetic radiation, said pulse having a duration which is short compared to the long decay lifetime, (c) detecting the fluorescent emission from said sample after the fluorescence of said ambient substances has substantially decayed, and (d) relating the fluorescence detected in (c) to the extent of specific binding reaction occurring in the solution.

In one particular embodiment, this invention provides a homogeneous assay which employs fluorescent background rejection in combination with the principle of energy transfer between two ligands, at least one of which is a chelating ligand capable of coordinating a rare earth metal ion to form the fluorescent chelate with a long decay lifetime and the other properties recited above. In such an embodiment the energy transfer is a function of the degree of specific binding which takes place and the energy transfer has the effect of varying the fluorescence and the degree of change in fluorescence is a function of the concentration of target entering into the specific binding reaction.

In another embodiment, this invention provides a homogeneous assay which employs an interligand transfer of a rare earth metal ion to form a changed-fluorescence complex as a result of the specific binding reaction. In this embodiment, the rare earth metal is presented as a chelate attached to one member of the specific binding pair, preferably the one with target-like properties, and the other member of the pair carries a ligand that is capable of forming the desired changed-fluorescence chelate with the rare earth metal. The second ligand should have the property of having a higher binding constant for the rare earth metal than the first ligand's so as to effect the desired metal transfer into the second chelate. In such an embodiment the extent of metal transfer is a function of the degree of specific binding which takes place and the metal transfer has the effect of varying the fluorescence and the degree of change in fluorescence is a function of the concentration of target entering into the specific binding reaction.

In a third embodiment of the present homogeneous assay method, a rare earth metal chelate is employed which contains a plurality of coordinating sites, not all of which are occupied by the chelate-forming ligand, and, as a result of the specific binding reaction, one or more of these unoccupied sites is filled by a ligand supplied by the specific binding partner so as to yield a new mixed ligand chelate of changed fluorescence. In this embodiment, the incoming ligand can displace the original ligand from some of the sites that it occupies in the original chelate. In such an embodiment the extent of mixed chelate formation is a function of the degree of specific binding which takes place and the mixed chelate formation has the effect of varying the fluorescence and the degree of change in fluorescence is a function of the concentration of target entering into the specific binding reaction.

DETAILED DESCRIPTION OF THE INVENTION

Reference to Related Applications

Several of the ligands which can be employed in the present invention are disclosed and claimed in U.S. patent application Ser. No. 712,774 of Hale and Solas filed Mar. 18, 1985, now U.S. Pat. No. 4,761,481, which is incorporated herein in its entirety by reference.

BRIEF DESCRIPTION OF THE DRAWING

In this description, reference will be made to the accompanying drawing in which the two figures illustrate energy transfer mechanisms which can take place in the present invention to provide the measurable change in detectable fluorescence.

DESCRIPTION OF PREFERRED EMBODIMENTS

Characteristics of the Fluorescent Chelates

Figure 1:
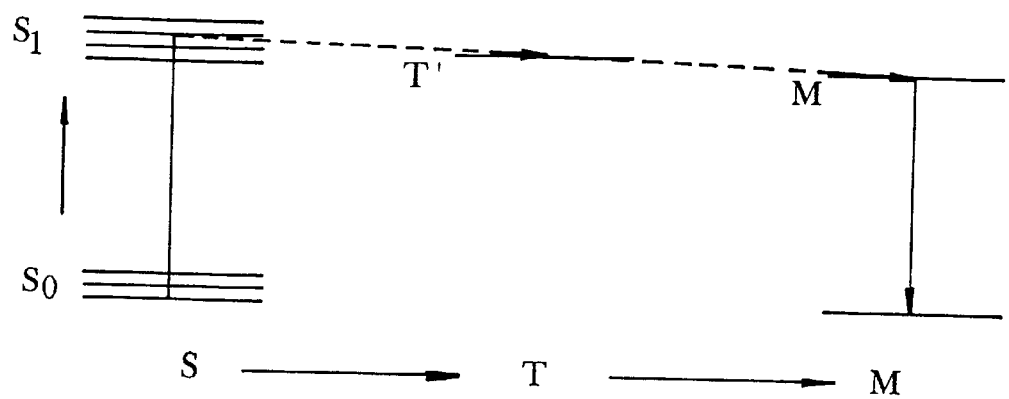

In the practice of the present invention, homogeneous assays are conducted with improved efficiency using fluorescent background rejection in combination with a measured fluorescent species that is a fluorescent chelate of a rare earth metal. The chelates are water-soluble, which can be defined as follows: the chelates must go into aqueous solution at pH's over the range of at least 6 to 10 at the concentrations employed in assays. While this concentration can in some cases be relatively low, it is preferred for processing and sample compatibility advantages that the chelate be soluble to at least $10^{-4}$ molar over this pH range. The chelates also should have stability in pH 6–10 aqueous media, as reflected by a metal to ligand binding constant ($K_{BC}$) greater than about $10^{13} M^{-1}$ (that is a log $K_{BC}$ of about 13 or greater) and exhibit a fluorescence that is long-lived (that is having a 0.01 msec or greater half life) and an intense quantum yield. Preferably it has a fluorescent excitation at a wave length of 300 nm or greater.

The fluorescent chelates used herein comprise a rare earth, i.e. lanthanide, metal ion. A wide range of rare earth metal ions can be used, including $Nd^{+++}$, $Pm^{+++}$, $Sm^{+++}$, $Eu^{+++}$, $Gd^{+++}$, $Tb^{+++}$, $Dy^{+++}$, $Er^{+++}$ and the like. Terbium ($Tb^{+++}$) and europium ($Eu^{+++}$) are the preferred rare earth metal ions.

Ligands useful for chelating with the rare earth metal ion are characterized by water solubility, high binding constants, and giving rise to chelates with quantum efficiencies greater than 0.01. A family of such ligands are the 2,6-bis[N,N-di(carboxyalkyl)aminoalkyl]pyridines. More particularly, a substituted aryl-substituted 2,6-[N,N-bis(carboxylalkyl)aminoalkyl]pyridine moiety which has the formula

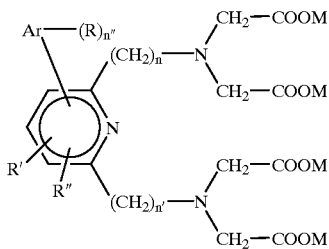

wherein n and n' are independently the integers 1 or 2, Ar is an aryl, n" is an integer equal to the number of available bonding sites on Ar, M is hydrogen or metal ion, and the n" Rs, R' and R" are each independently selected from hydrogen; electron-releasing groups including lower alkoxy, lower alkyl, amino, dialkylamino, aryl and aryloxy; and a linking group including a covalent bond and a bridge group capable of providing a link to the remainder of the molecule subject to the provisos that at least one of the n" Rs is an electron-releasing group and that at least one of R', R" and the n" Rs is a linking group to the remainder of the molecule. These materials are described in the above-incorporated application of Hale and Solas.

Other ligands which can form fluorescent chelates of appropriate stability and water-solubility include polyamine-polycarboxylic acids such as the diamine triacids of the formula

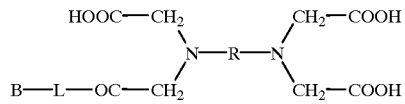

wherein B is the biospecific organic group, L is the link to the biospecific group and R is a two carbon or larger covalent organic bridge. These materials are disclosed in U.S. Pat. No. 4,432,907 of Wieder And Wollenberg which is incorporated herein by reference.

Yet another family of ligands which can take part in these homogeneous analyses are the substituted dipicolinic acids and salts of the formula

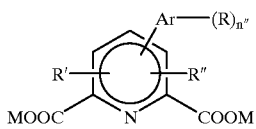

wherein one of the n" Rs, R' or R" is an antibody-like or a target-like moiety, the remaining members of the group of Rs, R' and R" are as described previously and the two Ms are independently selected from hydrogen and metal ions.

Other ligands include the triamine tetraacids of the formulae

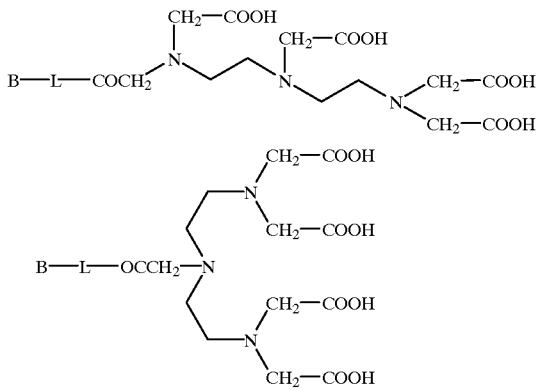

formed by the reaction of diethylenetriaminepentacetic acid in its dianhydride (Hnatowich, et al., INT. J. APPL. RADIAT. ISOT., 33, 327 (1982), activated mixed anhydride (Krejcarek and Tucker, BIOCHEM. BIOPHYS. RES. COMMUN., 77, 581 (1977), or active ester forms (Najafi, et al., INT. J. RADIAT. ISOT., 35, 554 (1984) with biospecific groups (B) containing suitably substituted linker groups (L).

Still other suitable-ligands include tetraacids of the formula

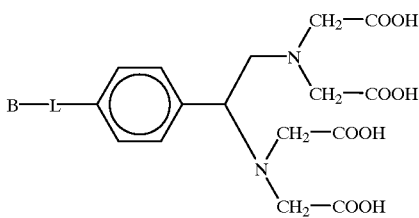

prepared from para-substituted phenyl ethylenediaminetetraacetic acids (Meares and Wensel, ACCOUNTS OF CHEMICAL RESEARCH, 17, 202 (1984) and imidate-linked tetraacids of the formula

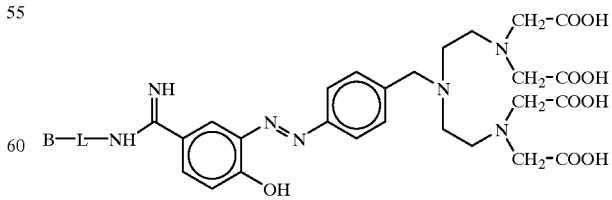

prepared from DTTA azo imidate (Paik, et al., J. RADIO-ANALYTICAL CHEMISTRY 57, 553 (1980).

The foregoing materials are representative. It is to be understood that the present invention is not dependent upon the use of any particular ligand or chelate but rather upon the use of rare earth chelates meeting the characteristics of solubility and stability set forth above.

The Links To The Biospecific Material

The fluorescent chelate is linked to a specific bindings material, that is, one half of a biospecific (e.g., immunologic) pair so as to permit biospecific assays to be conducted. The coupling of the fluorophore to the biospecific material can be a covalent chemical bonding or it can be an "antibody-antigen" type binding between the chelate and the specific binding material as is described in *Fluorescent Antibody Techniques and Their Application*, A. Kawamura, Ed., University Park Press, Baltimore, Md. 1969. The chelate-forming ligand moieties can be the site of linking to the biospecific groups. This linking can be accomplished by a covalent bond or through some other linking group either of which can constitute one of the R', R" or Rs, especially one of the Rs in the above described ligand structures.

When the linking is accomplished through a linking group this R group should present an active or bondable site such as an amine, a hydroxyl, a carboxyl, an ester or the like to facilitate coupling of the biospecific group. Examples of such bondable R groups are the amino group ($-NH_2$), primary and secondary amine terminated alkyls, primary and secondary amine terminated aryls and aryloxies, and the isomers thereof and the like; hydroxyl-containing alkyls, and hydroxyl-containing aryls and aryloxies.

Other suitable functionalities for forming a bond to the biospecific group include amides, amidines, thioamides, ureas, thioureas, guanidines, diazos, thioethers, carboxy and phosphate esters and thioesters and other covalent linkages such as are known in the art. A preferred linking group is the simple amino group. The linking groups can couple directly to the biologically active group or can be linked through a bifunctional spacer agent such as a member of the group

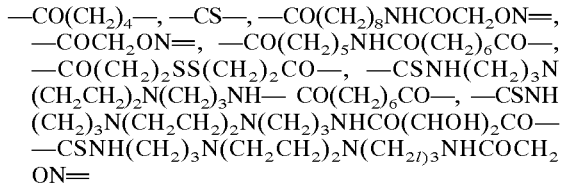

and the like. Such linking groups and spacer units are representative.

The Biospecific Group

As noted above, in the assays of this invention a biologically active. i.e., biospecific group is linked to the fluorescent chelate such as through the chelate-forming ligand. The terms "biospecific group" and "biologically active group" are used in a broad sense to encompass all molecular structures which will "specifically recognize" or "specifically react" or "specifically interact" with another molecular species. Such groups can include immunologically specific groups such as antibodies and their respective antigens or haptens, hormones, and their receptors, binding pairs such as the biotin/avidin pair and the like. They can also include nucleic acid sequences which will specifically hybridize with their complimentary sequences. The binding partners will be referred to generically from time to time as "antibody-like" and as "target-like" molecules.

The biospecific groups can be selected to bind with or otherwise associate with a target molecule or can be selected to mimic or to include the target molecule so as to compete with the target in the biospecific reaction.

It will be appreciated that to achieve the highest sensitivities it may be advantageous to purify the binding partners in terms of their biospecificity through application of affinity chromatography and like techniques.

The Analyte Molecule

The analyte or target molecule which corresponds to or interacts with the biospecific group may be a monoepitopic or polyepitopic material. In view of the water solubility properties of the fluorescent chelates required to be used in the present invention it is generally preferred if the target is a material which is found in aqueous-systems. It may be selected without limitation from materials such as drugs, metabolites, natural products, pesticides, chemicals and contaminants of air and water. For purposes of illustration, one can list drugs including digoxin, digitoxin, phenytoin, theophylline, gentamicin, and tobramycin; alkaloids such as morphine, heroin, cocaine, ergot alkaloids, and the like; steroids such as the steroid hormones including estrogens and androgens for example estriol and anti-inflammatory steroids for example cortisol; lactams such as the barbiturates including phenobarbital; aminoalkylbenzenes such as the amphetamines; vitamins, protaglandins such as $F_2$alpha and E, antibiotics and the like, short peptide sequences or amino acids such as thyroxine, triiodothyronine and oxytocin. Representative pollutants and pesticides include PCB, dioxin, halogenated biphenyls, carbamates, thiophosphites, phosphate esters and their metabolites. Such materials can range in molecular weight from about 50 to about 2000.

The target molecule can also be a polymeric material such as a protein or other polyamino acid, a polynucleic acid or a polysaccharide. Typical protein materials can be taken from any of the classes of proteins including without limitation globulins, albumins, lipoproteins, glycoproteins, histones and the like, hypersensitive proteins including albumin, the immunoglobulins such as IgE, fibrinogen, transferrin, the various complement factors, the tumor markers like CEA (carcinoembrionic antigen) and PAP, the various blood clotting factors and protein hormones including, beta-hCG, FSH, gastrin, LH and prolactin; insulin, thyrotropin, gonadotropin and the like. Examples of biospecific polysaccharides are those derived from microorganisms such as those associated with various species of Salmonella, Streptococcus, and Klebsiella. Other targets include without limitation materials responsive to infectious disease conditions such as infection with hepatitis or rubella.

The foregoing list is intended to be a brief outline. It is to be recognized that other equivalent materials such as are listed in more detail in the art (see, U.S. Pat. No. 4,193,983, columns 7–11 incorporated herein by reference) could be used in conjunction with the homogeneous fluoroassay techniques provided by this invention.

Reporter Mechanisms

In use in the homogeneous assays of this invention, a water-soluble rare earth chelate of the type above described is coupled to a specific binding reactant—either antibody-like or target-like— and comingled in an aqueous substrate with the other half of the specific binding pair which itself has the property of or is coupled to a group which has the property of varying the fluorescent emission of the rare earth chelate when the specific binding reaction has occured and brought the fluorescent chelate and the fluorescence-varying group into proximity. Set forth hereafter are a number of representative and, it is believed, novel analysis mechanisms which are made possible by the application of the present invention.

Energy Transfer-Quenching:

In one embodiment, the fluorescence-varying group can be a group which brings about energy transfer to or from the fluorescent chelate so as to enhance or to quench the fluorescence of the chelate.

Energy transferring fluorescence-varying groups include materials such as fluorescence-quenching metal ion complexes which draw energy away from a rare earth chelate when brought into close proximity with it and thus reduce its fluorescence. Period IV transition metal complexes, for example manganese, cobalt, iron and nickel complexes such as $Co^{++}$ in thermolysin or $Fe^{++}$ in transferrin complexes, will produce this effect when brought into proximity to a fluorescing rare earth complex such as a terbium chelate. Other compounds can exhibit this quenching property, as well. Representative examples of such materials are the rhodamines, for example, rhodamine B (Rh.B); substituted fluoresceins, for example, diether symmetrically substituted fluorescein;, phycobiliproteins and other quenching groups which meet the general requirement of good overlap of their absorption bands with the fluorophore's emission. These quenching materials may themselves fluoresce but at a wavelength and over a time course distinguishable from that at which the rare earth chelates themselves fluoresce.

Such quenching groups can be affixed to antibody-like or target-like groups so as to take part in biospecific reactions with the species to be quantitated and by the biospecific reactions brought into proper proximity with the fluorescent chelate so as to achieve quenching.

As an embodiment of this quenching mechanism, Rh.B can be interacted with a water-soluble fluorescent rare earth chelate, e.g. a terbium chelate. As noted by D. D. Thomas et al., PROC. NATL. ACAD. SCI., (USA), 75, 5746–50 (1978) when Rh.B is at an average distance of 65.7 Å from a fluorescent terbium chelate during the time that the chelate is in its excited state, 50% of the chelate's fluorescence is extinguished. Distances in the range of about 20 Å would be effective in the case of the Group IV metal complex quenching of rare earth metal chelate fluorescence, as well.

These are the types of distances between functionalities which are achieved in specific-binding interactions. Antibodies typically, have dimensions of about 35×65 Å for Fab fragments and 40×50 Å for Fc fragments. Day, E. D., ADVANCED IMMUNOCHEMISTRY, p. 108, Williams and Wilkins Co., Baltimore, Md., 1972. This means that if several rhodamine dye moieties are attached to an antibody, at least one rhodamine group will be close enough to at least partially quench the fluorescence of a fluorescent rare earth chelate coupled to the other member of the biospecific pair.

Quenching by energy transfer follows an $(r/R_o)^{-6}$ dependence, where r is the actual distance between donor and acceptor and $R_o$ is the distance for 50% transfer efficiency. Thus, to increase the quenching efficiency from 50% to 99%, one needs to bring the quencher to within about 30.6 Å of the chelate. This is a distance reasonable to achieve on an antibody-antigen or other biospecific reaction scale.

This distance is determined as follows:

$$K_{t=Ko}(r/R_o)^{-6}$$

where $K_t$ is the rate constant for energy transfer and $K_o$ is the sum of the rate constants for the decay of the excited donor in the absence of the acceptor.

Efficiency of Transfer=$K_t/(K_t+K_o)$ $K_t/(K_t+K_o)=0.99$ and $K_t=100K_o$.

To attain this value for $K_t$, r is calculated from the $(r/R_o)^{-6}$ dependence which shows $$K_t/K_o=100=(r/R_o)^{-6}(r/R_o)^{-1}=(100)^{1/6}=2.15$$

which means that if the donor and acceptor are 65.7 Å divided by 2.15 or 30.6 Å apart there will be 99% transfer of energy from donor to acceptor and the donor would be 99% quenched. Again, this is a dimension of a scale achievable in a biospecific reaction setting so that such high quenching efficiencies can be achieved. As previously noted, it is also possible to have more than one quenching group present on the biospecific reacting group. In such a case, in actual practice, quenching is obtained from the plurality of quenching groups and the quenching is the sum of quenching from all of the individual groups. This is very substantial even if no single group is brought to within precisely 20 or 30 Å by the biospecific reaction so long as the biospecific reaction does bring the quencher into relatively close proximity.

It will also be appreciated that the 99% quenching just described is in no way a requirement for the successful practice of this invention and that an assay would still be possible as long as there is a measurable decrease in fluorescence upon binding of AbL and TL molecules.

It should be realized that the foregoing are merely representative quenching systems and that other systems which provide the particular properties in the measured chelate as recited herein can also be employed with equal advantage.

As an example of a homogeneous assay using this quenching principle, a target-like molecule, TL, is labeled with a fluorescent terbium chelate and put into an aqueous solution with an unknown amount of target molecules. These are allowed to compete for a predetermined number of Rh.B.—labeled antibodies to the target. The fluorescence is measured after a predetermined incubation time. For large amounts of target material in the unknown sample there will be small amounts of quenching and vice versa. An inverse correlation binding curve can be established and used as a standard curve in the usual way.

As a direct-result of employing a stable soluble rare earth chelate as the fluorescent member of the pair, it is possible to readily apply fluorescent background rejection to the fluorescent measurement step. This entails using pulsed excitation and a delay in observation of the long-lived rare earth fluorescence until after background fluorescence has decayed. This results in greater sensitivity than can be attained with prior art homogeneous fluorescence-quenching assays because even small variations in fluorescence emanating from the rare earth chelate can be accurately measured as the substantial levels of interference are not a factor because of the background rejection.

It should be noted that because the antibody (or antibody-like molecule) can have several ligands (quenchers or fluorescers) attached to it, the assay works better with the quenchers on the antibody-like molecules so that nonparticipating quenchers add nothing to background. If the fluorescer were on the antibody or antibody-like molecules, then nonparticipating fluorescers would contribute a background of fluorescence which would need to be subtracted. While this is possible in principle, it is clearly advantageous to have the quenchers on the antibody-like molecules rather than fluorescers.

One combination of a fluorescent chelate-quencher pair mentioned above is the pyridyl-tetraacetic acid I and rhodamine II shown below.

I

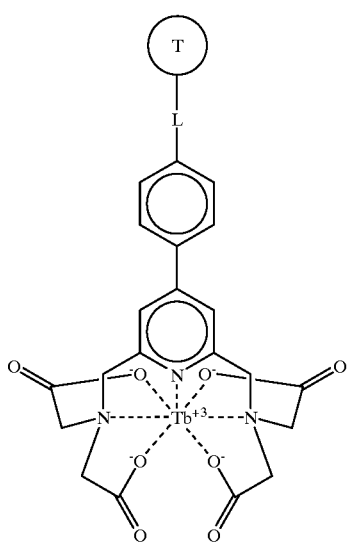

II

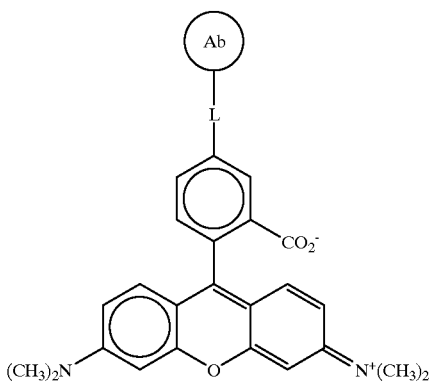

A second fluorescer-quencher combination is the substituted phenanthroline tetraacetic acid terbium chelate III and rhodamine B.

III

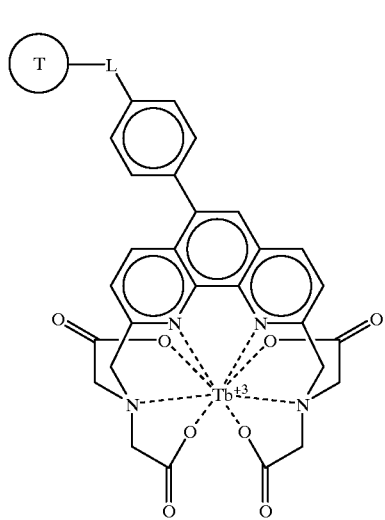

Yet a third representative fluorescer-quencher combination would be the tetraacid I together with the antibody-linked quencher of the formula

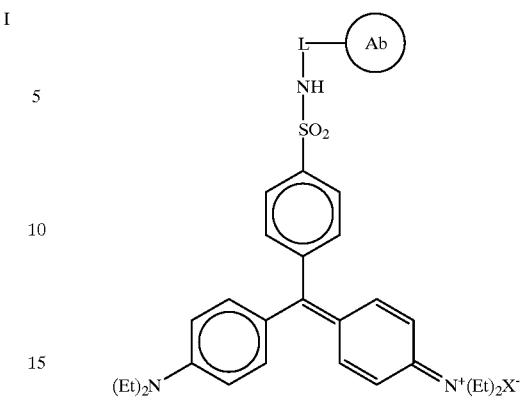

Energy Transfer-Activation:

The present homogeneous assay process can also function in a "light up" or "activation" mode wherein a rare earth chelate is employed which, when attached to its target-like or antibody-like group, has substantially reduced fluorescence for a specific range of excitation wavelengths employed. The binding constant of the rare earth metal to the ligand of this chelate must be greater than about $10^{13}M^{-1}$ so that the metal will not fall out even at the highest dilutions and under all conditions of the assay. One example of a class of useful chelating ligands with this property is the pyridyl tetraacids disclosed in the above-noted United States Patent Application of Hale and Solas. A molecule consisting of a target-like group coupled to such a tetraacid and carrying a rare earth ion can be excited upon binding to its antibody-like binding partner by energy absorbed from the antibody-like group itself or from an activating group attached to it. Such a chelate can be activated or caused to "light up" when brought into proximity, by reason of the biospecific reaction, with an activator group which is capable of positive energy transfer to it.

Figure 2:
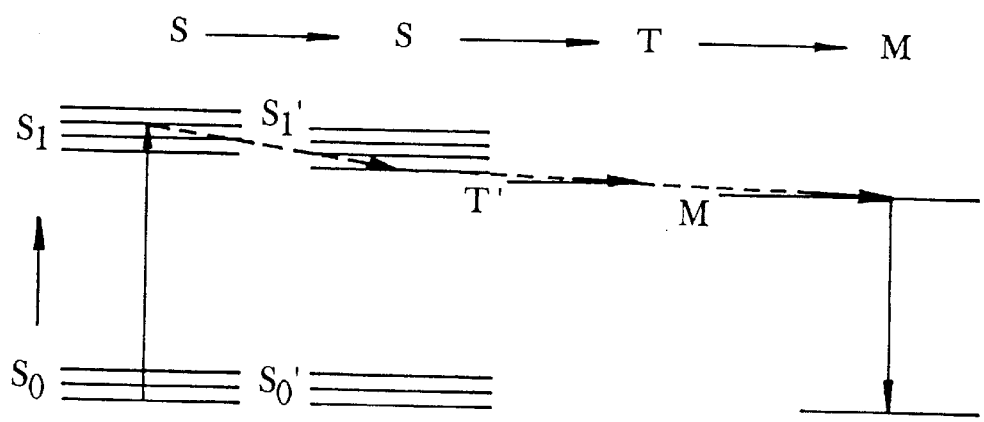

This positive energy transfer can be effected by either of two excitation mechanisms as are shown in FIGS. 1 and 2. Classically, it has been viewed that energy transfer to rare earth metals from exciting ligands occurs via a singlet (S) in the activating group transferring energy intramolecularly to a triplet (T) in the activated group which in turn transfers energy intramolecularly to the metal which then gives up the energy in the form of fluorescence. Heller and Wasserman, J. PHYS. CHEM., 42, 949, 1965. This singlet-triplet-metal or "S-T-M" route is shown schematically in FIG. 1, as $S_o S_1 T^1 M$. The S-T-M method, while in theory usable, has the disadvantage in the present setting that the distance separating the exciting group and the excited group must be very small–on the order of 5 Å or so. This follows directly from the fact that the distance for 50% efficient energy transfer "$R_o$" is proportional to $(Q_o)^{1/6}$ wherein $Q_o$ is the quantum efficiency and in the case of triplets $Q_o$ is $10^{-6}$ or less. Thus, for this mechanism to be really effective, the spacing of the energy transfer partners must be closer than the usual dimensions encountered in antibody-antigen interactions and other biospecific reactions.

It has now been found that a second activation or "light up" energy transfer mechanism can be used. - In this mechanism, energy is transferred from a singlet in the donor to a singlet in the acceptor then to a triplet in the acceptor and finally to the metal. This S-S-T-M mechanism is shown in FIG. 2 (as $S_o \rightarrow S_1 \rightarrow S_1'$ (associated with $S_o'$)$\rightarrow T' \rightarrow M$) and is advantageous because the intermolecular transfer is a transfer which can have $R_o$ values in the 50 Å range which are dimensions routinely encountered in biospecific reactions.

Examples of soluble and stable rare earth metal chelate-energy donor pairs which can work to effect this activation or light up mechanism are in Table 1.

TABLE 1

| Rare Earth Chelate | Activator |
|---|---|
| Rare earth metal chelate of tetraacid of the formula [structure shown with Ar—(R)$_{n''}$, (CH$_2$)$_n$—N(CH$_2$—COOH)$_2$, pyridine ring with R', R'', (CH$_2$)$_{n'}$—N(CH$_2$—COOH)$_2$] Where one of the Rs includes theophylline | Anti-theophylline antibody |
| The rare earth metal chelate of the above formula [structure shown: I—T aryl group connected via carbonyl to chromene system with bis(aminomethyl) groups chelating Tb$^{+3}$ with four CO$_2^-$ groups] | An antibody containing a suitably situated tyrosine or tryptophan residue in its structure Ab—L—NH—CH$_2$—CH$_2$—CO—NH—[phenyl-oxazole-phenyl structure] |

In such systems, when the chelate and activator are present in an aqueous solution the biospecific reaction has the effect of bringing the activator and chelate into proper proximity for activation or "light up" to take place and thus the extent of fluorescence is a measure of the extent of the biospecific reaction. Thus, again, analysis sequences which involve competition for one half of the biospecific pair by the other and an analyte in the test liquid can provide a measure of the concentration of the analyte.

Metal Transfer:

Water-soluble rare earth metal chelates can also participate in homogenous assays by employing the mechanism of interligand metal transfer. This aspect of the invention relates to the process in which the occurrence of the specific binding reaction of the target-like molecule with the antibody-like molecule leads to transfer of the rare earth metal directly from one member of the specific binding pair to the other. This transfer results in a change in the environment of the rare metal which is observed as a change in its fluorescent properties as measured by application of the techniques of fluorescent background rejection set forth in U.S. Pat. No. 4,058,732.

In order to accomplish this metal transfer and accompanying change in fluorescence, one member of the binding pair is coupled to a first chelating ligand via a suitable linking group or functionality. The second member of the binding pair is likewise coupled to a second chelating ligand. The occurance of the biospecific reaction brings the two ligands into proximity with one another such that the direct transfer of the rare earth metal from one chelate structure to the other can take place. It is known that metals can be transferred from one chelating group to another (Bates et al. J. BIOL. CHEM., 242:2810 (1967)), especially one with a higher binding constant and rate constants of the process have been measured. In other studies (Margerum et al. J. AMER. CHEM. SOC., 87:4463 (1965)), the displacement of one metal from EDTA-type chelates by another metal having a higher binding constant was found to proceed in a stepwise fashion with the release of coordinating groups from the first metal being followed by their coordination to the second metal. This implies that for a finite period of time during the displacement, a ternary complex is formed with both metals. By analogy, with two ligands competing for a single metal, it is expected that a transitory ternary complex will be formed, thus imposing the requirement that the linking group or functionalities coupling each chelating group to its respective member of the binding pair be sufficiently long and flexible to allow contact of the two ligands once the binding reaction has taken place. This mechanism requires that there be actual transfer of the metal from one chelate into another. This is distinguishable from methods in the art wherein a metal is complexed, released from the complex into solution by a pH change or the like and then recomplexed with a second ligand.

Both of these ligands have the properties of forming the water-soluble stable complexes called for herein. It is important to stress the stability property of the two chelates in this setting. Both of the chelates must be strong enough to hold the metal at high dilutions and in the presence of serum components and the like which could compete for the metal ions.

In this mechanism, the second ligand, that is the receiving ligand, must have the property of forming a complex with the rare earth metal which has a higher level of stability than does the complex with the first, or donating, ligand. Preferably these stabilities are at least about one order of magnitude different and more preferably at least about two orders of magnitude different. Expressed numerically, log $K_{BC2}$–log $K_{BC1}$=at least 1 and
preferably at least 2, wherein $K_{BC2}$ is the metal-ligand stability constant for the chelate being formed and $K_{BC1}$ is the same constant for the chelate giving up the metal.

This mechanism can work in a quenching analysis or in an enhancement analysis depending upon the change in fluorescence detected between the first and second chelates. It is generally preferable for the second chelate to be the more fluorescent so as to provide a more easily detected enhancement assay method. Also, as noted previously, it may be of advantage to have spacers or leashes between the biospecific groups and the respective ligand functionalities so as to facilitate close approach between the receiving ligand and the donating chelate.

In summary, the properties preferred in the first ligand are that it form chelates which are relatively nonfluorescent when excited in a specific wavelength range and capable of binding a rare earth ion strongly enough to retain it under assay conditions of high dilution and the presence of serum components. The second ligand preferably should form metal chelates which are highly fluorescent and which bind the metal with a binding constant much higher than that of the first ligand. In addition, the combined length of the linking functionalities coupling the ligands to the respective members of the binding pair must be sufficient to allow good contact following the binding reaction.

While either ligand may be coupled to either member of the binding pair, in preferred embodiments the first ligand is coupled to the target-like molecules and chelates the rare earth ion tracer while the second ligand is coupled to the antibody-like molecules. Small target-like molecules will generally be coupled to a single first ligand, although larger analytes may be multiply labeled. The antibody-like molecules will generally be labeled with several second ligands. At the concentrations used in immunoassays (on the order of $10^{-8}$M or less) transfer of the metal from the first ligand to the second ligand would be a very slow process in the absence of a specific binding reaction between the member of the binding pair. Indeed, a specific pair of first and second ligands not coupled to target-like or antibody-like molecules were found to require many hours for detectable metal transfer to occur at $10^{-9}$M where transfer is dependent on diffusion and random collisions, while at $10^{-5}$M and higher concentrations, transfers of metal occurred rapidly. Thus, in an assay for the target analyte, the specific binding reaction of the first chelate-labeled target-like molecule to the second chelate-labeled antibody-like molecule creates a locally high effective concentration leading to transfer of the metal to the second chelate and the accompanying increase in fluorescence emission.

The basis for an assay for the target analyte is then competition between an unknown concentration of target molecules and the labeled target-like molecules for binding to the labeled antibody-like molecules. This competition occurs during an incubation period and the fluorescence is then read directly without any separation step using the principles of fluorescence background rejection as outlined in U.S. Pat. No. 4,058,732.

As representative specific embodiments of ligands which can participate in this metal transfer mechanism one can employ

| Donating Rare Earth Chelate | Receiving Ligand |
|---|---|
| Rare earth metal chelate of triacid of the formula<br><br>HOOC—CH$_2$　　　　CH$_2$—COOH<br>　　　　＼　　　／<br>　　　　　N—R—N<br>　　　　／　　　＼<br>T—L—OC—CH$_2$　　　CH$_2$—COOH<br><br>Wherein T is a target-like molecule and L is a linking group as shown in U.S. Pat. No. 4,352,751 | Antibody-linked phenanthroline tetraacetic acid |
| Rare earth metal chelate of the above triacid | Antibody-linked phenylpyridine tetraacetic acid |

Mixed Ligand Mechanisms:

This is a mechanism in which two chelating ligands are used. The first ligand has the property of forming a stable water-soluble complex with the rare earth metal. This first chelate should be relatively nonresponsive to excitation in the wavelengths of interests so as to be relatively nonfluorescent. The first ligand should also have the property that it does not utilize the total number of coordinating sites of the metal thus allowing a second ligand to coordinate as well. (See, F. R. Haddad, TALANTA, vol 1, 1–13 (1977).) The second ligand should have the property of being able to coordinate these remaining sites on the rare earth metal even though it is already being held by the first ligand and thereby forming a complex having increased fluorescence in the desired wavelength range.

This sharing of the metal by the two ligands will only occur to a large extent when the two ligands are brought into close proximity by reason of a biospecific reaction between antibody-like and target-like groups to which they are attached. Thus, the detected change in fluorescence properties is a measure of the extent to which the biospecific reaction has occurred. As in the case for metal transfer, the ligands may be joined to the biospecific groups through spacers and the like to achieve proper spacing for the two ligands to complex with the rare earth metal.

As specific embodiments of this mechanism one can employ the above-described diamine triacid chelates or the di- and triamine tetraacid chelates described earlier as the first chelate. An antibody-linked substituted dipicolinic acid can function as the second ligand. These embodiments are merely representative. Other equivalent materials could be employed as well.

This mechanism is largely the same as in the metal transfer case, with the distinction being that both ligands remain in complex combination with the rare earth metal in this case while in the metal transfer case the first ligand is free from the metal after the transfer has taken place.

The invention is further illustrated by the following Examples. These are presented to describe representative preparations of materials useful in the prectice of the invention and to illustrate various representative embodiments of the invention and are not to be interpreted as limiting the invention's scope.

EXAMPLE 1

Preparation of Aryl-Substituted Pyridine Ligands

The process of this Example, which is based upon the teachings of USSN 712,774 of Hale and Solas, is used to prepare a family of aryl-substituted pyridyl tetraacid ligands. These ligands have the general structure

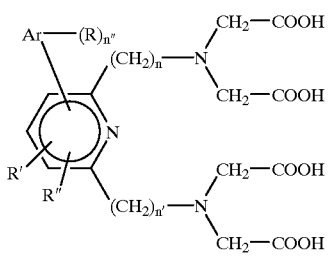

wherein n and n' are independently the integers 1 or 2, Ar is an aryl, n" is an integer equal to the number of available bonding sites on Ar, and the n" Rs, R' and R" are each independently selected as set forth hereinabove and especially from among hydrogens, alkoxies, amines and isothiocyanates. In a representative preparation the following reactions are carried out:

A. 1,5-di(2-furyl)-3-phenyl-1,5-pentanedione

| Benzaldehyde | 62.6 g (60 ml) (0.59 mols) |
| 2-Acetyl furan, 85% | 165 g (150 ml) (1.27 mols) |
| Potassium hydroxide, 85% | 35 g (0.53 mols) | are reacted at 60° C. Following reaction, product crystals are recovered. Yield of pentanedione, 103.5 gms or 57.3%.

B. 4-Phenyl-2,6-di(2-furyl)pyridine

| 1,5-Di(2-furyl)-3-phenyl-1,5-Pentaedione | 143 g |
| Hydroxylamine hydrochloride | 129 g Aldrich 102337 |
| n-Butanol | 1600 ml Sigma 13F-5070 |

The "dione", as produced in step A. the hydroxylamine and the butanol are combined, refluxed and stirred, cooled and stirred for about 60 hours. The resulting black solution is worked up to yield about 79 g of product crystals.

C. 4-Phenyl-2,6-pyridinedicarboxylic acid

The difuryl pyridine product of step B. is oxidized with permanganate.

| Product of Step B | 23 mmoles |
| $KMnO_4$ | 45.4 grams |
| t-Butanol | 1500 ml |
| Water | 300 ml |

The product of step B is added to the t-butanol. The mixture is heated and stirred then the $H_2O$ is added and the $KMnO_4$ is added in portions over about 30 minutes at 75° C. The mixture is refluxed for 90 minutes. The product is worked up to give crystals of the desired 4-phenyl-2,6-pyridinedicarboxylic acid. The dicarboxylic acid which results is useful in its own right as a ligand in the formation of water-soluble chelates of the rare earth metals and also is useful as an intermediate in this reaction sequence.

D. 4-Phenyl-2,6-pyridinedicarboxamide

| 4-Phenyl-2,6-pyridine-dicarboxylic acid | 21.5 mmoles |
| Oxalyl chloride | 4.8 ml |
| Methylene chloride | 80 ml |
| Dimethylformamide | 5 drops |

The pyridinedicarboxylic acid is added to the $CH_2Cl_2$, and DMF. The flask is closed with a $CaSO_4$ drying tube, and cooled in ice. The oxalyl chloride is added gradually. The resulting solution is concentrated and added to $NH_4OH$, 28%, over 5–10 minutes with stirring, stirred for an hour, filtered and washed with water and dried to give the desired amide.

E. 4-Phenyl-2,6-pyridinedicarbonitrile

| 4-Phenyl-2,6-pyridine-dicarboxamide | 17.5 mmoles |
| p-Dioxane | 170 mls |
| Pyridine | 11.3 ml |
| Trifluoroacetic anhydride | 11.0 ml |

The first three ingredients are combined and cooled to 10°. The anhydride is added and the mixture is stirred for two hours at room temperature. The resulting dark solution is worked up to give the desired dicarbonitrile.

F. 4-Phenyl-2,6-di(aminomethyl)-pyridine

| 4-Phenyl-2,6-pyridine-dicarbonitrile | 13.5 mmoles |
| Ethanol with 2% $HClO_4$ | 370 ml |
| 10% Palladium on carbon | 3.7 g |

The nitrile is suspended in the ethanol and $HClO^-_4$. The catalyst is added and the system is then pressured to 40 psi with hydrogen. After 30 minutes a yellow solid is recovered by precipitation and dissolved in water and NaOH. The liberated amine that results is recovered as a dark oil.

G. 4-Phenyl-2,6-bis[N,N-di(methoxycarbonylmethyl)-aminomethyl]-pyridine

| Amine of Step F | 12.0 mmole |
|---|---|
| 1,8-Bis(dimethylamino)-naphthalene | 10.3 g |
| Methyl bromoacetate | 7.35 g |
| Acetonitrile | 130 ml |

The base, amine and acetonitrile are stirred. Then the methyl bromoacetate is dripped in. After about 16 hours at about 45° C., the product is worked up to give the desired ester.

H. Saponification of Tetraester

The tetraester of Step G is saponified in methanol/water, 1:1, and $K_2CO_3$. The solution is acidified to pH 7, and dried to give the desired tetraacid ligand. In additional preparations this process is repeated but using different aldehydes, thus forming different tetraacids.

EXAMPLE 2

Preparation of Diamine Triacids

These materials are prepared using the process set forth in U.S. Pat. No. 4,352,751.

EXAMPLE 3

Preparation of Phenanthroline Tetraacetic Acid Ligands

These materials are prepared using the process set forth in European Patent Application 0068875 (Eastman Kodak).

EXAMPLE 4

An Energy Transfer Fluorescence Enhancement Homogeneous Assay

A. 2,6-bis[N,N-di(carboxymethyl)amino- methyl]-4-(4-nitrophenyl)-pyridine tetramethyl ester Fuming nitric acid (0.03 ml, 0.4325 mmol) is added at room temperature to a solution of trifluoromethanesulfonic acid in methylene chloride (4 ml). After stirring for 5 minutes, a solution of 2,6-bis-[N,N-di(carboxymethyl) aminomethyl]-4-phenyl-pyridine tetramethyl ester such as from step G of Example 1 (86 mg, 0.173 mmol) in a small amount of methylene chloride is slowly added at 0° C. The solution is allowed to warm to room temperature and stirring is continued for one hour. The reaction mixture is then poured onto ice and the mixture is neutralized with sodium carbonate. Extraction with methylene chloride followed by drying over sodium sulfate and evaporation gives 90 mg of crude product.

B. 2,6-bis[N,N-di(carboxymethyl)-aminomethyl]-4-(4-aminophenyl)-pyridine tetramethyl ester The crude product from the above reaction (90 mg, 0.17 mmol) is dissolved in ethanol (13 ml), 10 mg of 10%- Pd/C is added and the mixture is stirred at room temperature under one atmosphere of hydrogen for one hour. The catalyst is removed by filtration and the solvent evaporated to give 60 mg of the 4-amino compound. The 3-amino compound (51 mg) is prepared similarly from 70 mg (0.129 mmol) of the corresponding 3-nitro compound. If desired, these or similar aryl pyridines having amine substituents on their aryl rings can be reacted with thiophosgene to convert the amine to an isothiocyanate which in turn can couple to amine-containing target molecules or the like.

C. Conjugation of 2,6-bis[N,N-di(carboxymethyl) aminomethyl]-4-(4- and 3-aminophenyl)-pyridine tetramethyl esters to theophylline-8-butyric acid Isobutylchloroformate (0.02 ml, 0.117 mmol) is added to a solution of theophylline-8-butyric acid (31.3 mg, 0.117 mmol) in dimethylformamide (1.5 ml) containing triethylamine (0.20 ml, 0.117 mmol) at 0° C. under an argon atmosphere. After 0.5 hour at 0° C., a solution of the 4-amine (60 mg, 0.117 mmol) in chloroform is slowly added. The solution is stirred for 17 hours at 0–5° C. and then the solvents are removed by evaporation to leave 103 mg of crude product. The material is chromatographed on silica gel with chloroform:methanol (9:1) and on reverse phase C-18 silica gel with methanol:water (7:3) to give 60 mg (67% yield) of the desired product. The corresponding 3-amino compound (51 mg, 0.10 mmol) is treated similarly to give 50 mg of material having the theophylline derivative conjugated at the 3-position.

D. 2,6-bis[N,N-di(carboxymethyl)-aminomethyl]-4-[4-(-theophylline-8-butyramido)-phenyl]-pyridine tetraacid The tetramethyl ester (34 mg, 0.045 mmol) from the previous step is dissolved in methanol (2 ml) containing 0.2 ml of 1 N sodium hydroxide and heated at reflux for three hours. The solution is then cooled in an ice bath and acidified with 1 N HCl and evaporated to give the crude product. Purification via reverse phase column chromatography in methanol:water (6:4) gives 14 mg of the tetraacid. Saponification of 40 mg (0.05 mmol) of the analogous 3-substituted compound gives 14.6 mg of its tetraacid after reverse phase chromatography.

E. Preparation of Chelates

The tetraacids of Part D are separately dissolved in 0.01M sodium borate solution to a concentration of $10^{-5}$M. Then an equivalent molar amount of aqueous terbium chloride is added to each and the mixtures are allowed to stand for a few minutes. Fluorescence measurements are carried out and demonstrate that 1:1 molar chelate complexes of the tetraacids and the terbium have been formed and that such complexes are fluorescent and stable.

F. An Energy Transfer Fluorescence Enhancement Assay

An assay for theophylline is carried out by allowing the terbium chelate of the fluorophore-labeled theophylline tracer above (i.e., 2,6-bis[N,N-di(carboxymethyl) aminomethyl]-4-[4-(theophylline-8-butyramido)-phenyl]-pyridine terbium chelate) to compete with theophylline standards for binding to antitheophylline antibody. The labeled theophylline on binding to antibody undergoes an enhancement of its fluorescence and this enhancement is proportional to the amount of labeled theophylline bound and inversely proportional to the amount of theophylline present in the sample. The assay is carried out in polystyrene tubes (12×15 mm) to which 1 ml of pH 8.5 0.01M sodium borate buffer was added. This is followed by the addition of 10 μl of 1 μM tracer (8.7 ng) and 10 μl of theophylline standard (0, 5.4, 16.2, 54, and 540 ng). Addition of 25 μl of about 0.3 μM anti-theophylline antibody in 0.01M borate containing 0.1M sodium chloride and 1% normal human serum (final concentration in assay tube about 7.5 nM) leads to increases in the observed fluorescence of 400%–50%, respectively, for the various standards. This corresponds to $B/B_o$ values of 80, 64, 53 and 14% for the 5.4, 16.2, 54 and 540 ng standards, respectively.

EXAMPLES 5

An Energy Transfer Fluorescence Quenching Assay

This Example demonstrates the application of the principles of an energy transfer homogeneous assay of the fluorescence-quenching type in which the target-like molecule is a fluorescent chelate of terbium and the antibody-like molecule is an anti-target antibody to which has been conjugated a suitable quencher. Specifically, following the process generally shown in Example 1 and specifically set out in Example 18 of U.S. patent application Ser. No. 712,774, the ligand tetraester 1 shown in Reaction Sequence 1, below, is prepared in nine steps from 3-nitro-benzaldehyde and 1-acetylfuran. This material is then coupled to the target analyte phenyltoin via an eight carbon linking group by reacting 3-(7-carboxyheptyl)-5,5- diphenylhydantoin 2 with 1 using 1-ethyl-3-(3-N,N-dimethylaminopropyl)-carbodiimide and N-hydroxysuccinimide. The resulting tetraester is saponified to give the ligand-labeled phenyltoin analog which is chelated with terbium to give the tracer 3. This highly fluorescent compound has an emission maximum at 544 nm and is ideally suited for energy transfer to rhodamine-B which has an absorption maximum at 544 nm. Thus, the antiphenytoin antibody may be labeled with TRITC (tetramethylrhodamine isothiocyanate) following procedures known in the art (FLUORESCENT ANTIBODY METHODS, Academic Press, New York (1968)) to give the quencher-labeled antibody-like member of the specific-binding pair. The specific binding which occurs on mixing the two members of the specific-binding pair brings the fluorescer and quencher within the distance required for energy transfer to occur and the amount of quenching is inversely related to the amount of phenyltoin present in the sample.

EXAMPLE 6

An Energy Transfer Fluorescence Enhancement Assay

This Example demonstrates the application of the principles of an energy transfer homogeneous assay of the fluorescence-enhancement type in which the target-like molecule is a fluorescent chelate of europium and the antibody-like molecule is an anti-target antibody to which has been conjugated a suitable enhancer. Specifically, following the process of European Patent Application 0068875 (Eastman Kodak), the fluorophore ligand 4 is prepared and as shown in Reaction Sequence 2, below, is coupled to the theophylline analog 5 using 1-[3-(N,N-dimethylamino)-propyl]-3-ethyl-carbodiimide (EDAC) and N-hydroxysuccinimide (NHS). The resulting product is saponified and chelated to europium to give the target-like member 6 of the specific binding pair.

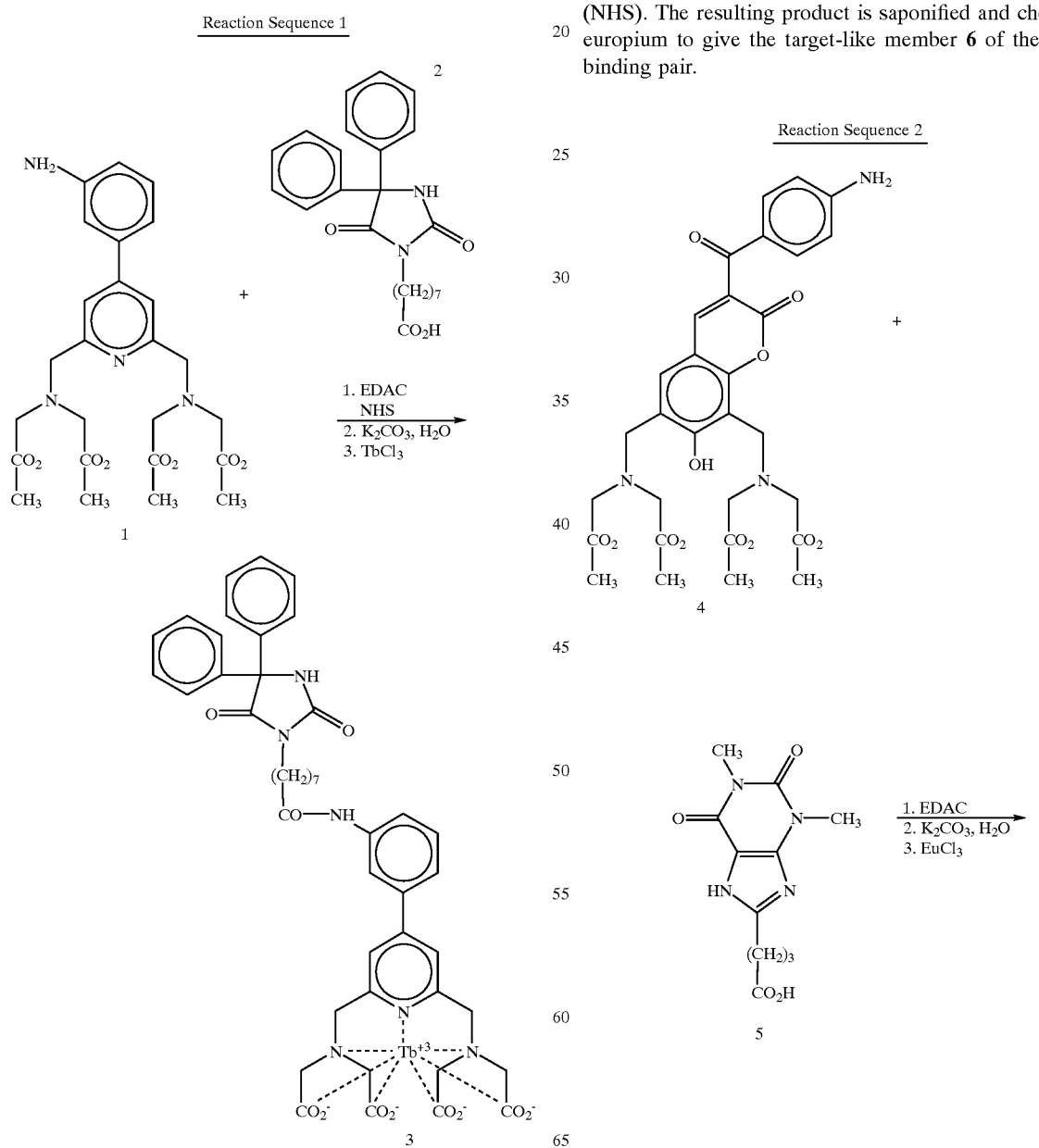

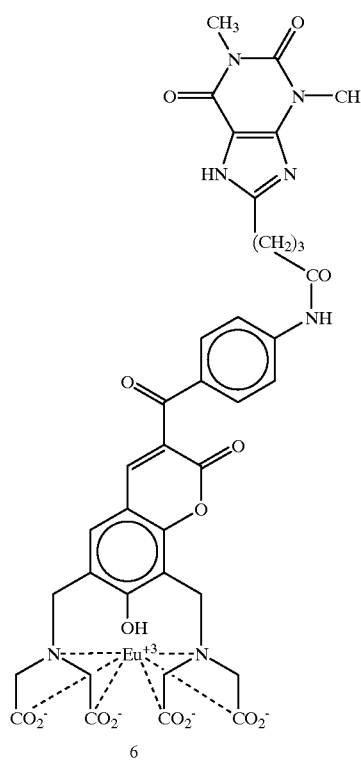

6

Preparation of the antibody-like member of the specific binding pair involves preparation of a suitable enhancer label with a functional group for conjugation to an anti-theophylline antibody. Such a label is prepared as shown in Reaction Sequence 3, below, by nitration of 2,5-diphenyloxazole (PPO) with nitronium trifluoromethane-sulfonate. The resulting 2-phenyl-5-(4-nitrophenyl)-oxazole is reduced with hydrogen and 10% palladium-on-carbon catalyst to give the corresponding 2-phenyl-5-(aminophenyl)-oxazole (amino-PPO, 7). The amino group is coupled to N-CBZ-B-alanine using oxalyl chloride and the benzyloxycarbonyl protecting group is removed by hydrogen and Pd/C to give B-alanyl-PPO 8. Conjugation of 8 to anti-theophylline is accomplished by means of the homobifunctional cross-linking agent BS$^3$ (bis-sulfosuccinimidyl suberate) and the product is purified on an affinity column (theophylline-8-butyric acid on AH Sepharose) to give the antibody-like member 9 of the specific binding pair. The fluorescent emission maximum of the PPO fluorophore attached to the antibody is at 412 nm and overlaps well with the excitation maximum of 394 nm for the theophylline derivative 6. Following the binding reaction, the PPO enhancer and the rare earth chelate fluorophore are brought within the distance required for efficient energy transfer to occur and the amount of enhancement of the rare earth emission is inversely proportional to the amount of theophylline in the sample being assayed.

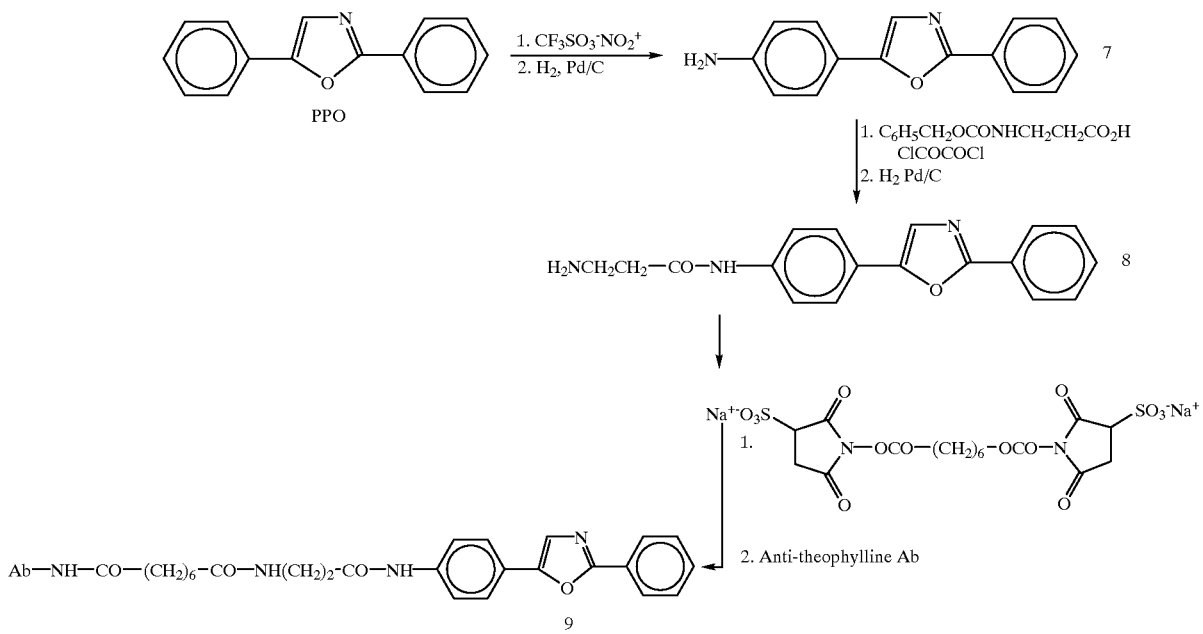

EXAMPLE 7
Preparation of a Theophylline-linked Triacid First Chelate For Use in Homogeneous Assays Following the reaction scheme shown in Reaction Sequence 4, below, theophylline-8-butyric acid (10, 210 mg, 0.79 mmole) is dissolved in dimethylformamide (DMF, 8- ml) and the solution cooled in an ice bath to 0° C. Triethylamine (72.6 mg, 0.72 mmole) is then added, followed by isobutyl chloroformate (95 mg, 0.69 mmole) and the solution is stirred at 0° C. for 30 minutes during which time a white precipitate forms and intermediate mixed anhydride 11 is produced. Ethylenediamine (620 mg, 10.3 mmole) is added to give a clear solution which is stored overnight at 0° C. The mixture is then concentrated on a rotary evaporator at 70–80° C. and the residue is triturated with diethyl ether. The resulting oily solid residue is recrystallized from ethanol chelate 14a (m.p. ~130–160° C. dec.). Similarly, homologs 14b and 14c are prepared from 1,6-diaminohexane and 1,10-diaminodecane.

In addition, other analogs are prepared by use of such diamine linking groups as bis-2-aminoethyl ether, 1,2-bis(2-aminoethoxy)ethane and N,N-bis(3-amino propyl) piperazine.

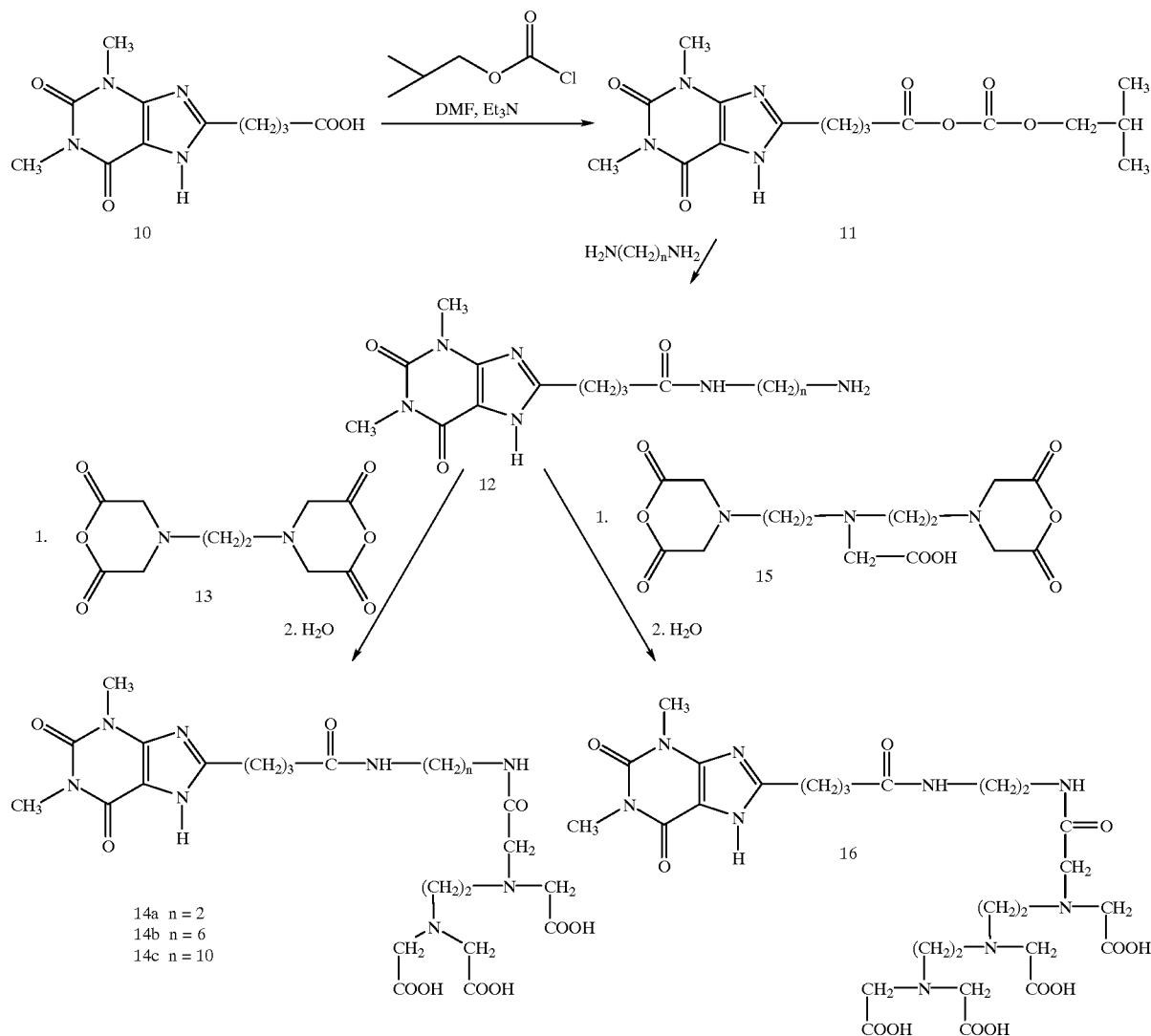

Reaction Sequences 4 and 5 to give 160 mg (0.52 mmole, 75% yield) of theophylline derivative 12, m.p. 199–201 (dec.).

12 (155 mg, 0.51 mmole) and ethylenediamine-tetraacetic acid dianhydride (13, 300 mg, 1.17 mmole) are dissolved in DMF (10 ml) and heated at 65° C. for 3 hours. Water (1.5 ml) is then added and heating continued for 1.5 hours followed by cooling at 0° C. The precipitate (EDTA, 134 mg) which forms is removed by filtration and the filtrate is concentrated on the rotary evaporator. The residual syrupy oil is triturated with acetone (40 ml) and the resulting solid is twice recrystallized from ethanol (40 ml) to give 119 mg (0.2 mmole, 40% yield) of the theophylline-linked triacid EXAMPLE 8
Preparation of Theophylline-linked Tetraacid First Chelate for Use in Homogeneous Assays Following the reaction scheme set forth in Reaction Sequence 5, above, intermediate 12 (164 mg. 0.53 mmole) is dissolved in DMF (3 ml) and slowly added to a stirred solution of diethylenetriaminepentaacetic dianhydride 15 in DMF (5 ml) and heated at 65° C. for 2 hours. After two hours, TLC indicates the disappearance of 12 and water (1.0 ml) is then added and heating continued for 40 mintues. After cooling to room temperature overnight a precipitate (DTPA, 220 mg) which forms is removed by filtration and the filtrate is concentrated on a rotary evaporator. The viscous residue is triturated with acetone. The resulting solid partially dissolves in hot ethanol. Additional DTPA is removed and the filtrate is cooled to crystallize the desired product 16. Addition of diethyl ether to the filtrate gives a second crop of solid. Total yield 190 mg, m.p. 129–160, decomposition with loss of carbon dioxide.

EXAMPLES 9–12
Preparation of Antibody-linked Second Ligands (9) This preparation follows Reaction Sequence 6. In the first reaction, 5.16 μl (1 μmol) of a chloroform solution of 4-amino-tetraester 17 of Part B of Example 4 is placed in a reaction vial. Solvent is evaporated under argon. One ml of methanol is added followed by 4 μl of 1 N NaOH in methanol. The reaction mixture is stirred overnight at room temperature. Then 50 μl of 20 mM SPDP in ethanol (1 μmol) is added with stirring. The reaction proceeds for one hour to yield 18. One μmol of DTT in ethanol is added and stirred for one hour after which solvent is evaporated to yield ligand 19. Ten μmols of affinity chromatography-purified anti-theophylline antibody, identified as lot number "CA #007" is diluted to 750 μl with 10 mM phosphate buffered saline (PBS). Then 116 μg (0.37 μmol) of SPDP is added and reacted with stirring at room temperature for 45 minutes to yield leashed antibody 20 which is recovered by ultrafiltration. 400 μmols of ligand 19 are then mixed with antibody 20 in methanol and water in a molar ratio of ligand to antibody of about 40:1 and stirred overnight at room temperature to obtain ligand-labeled antibody 21. Based on the projections in PROC. NATL. ACAD. SCI., 77, 4539, (1980), one might expect there to be about four ligand attachment sites per antibody, on average. The reaction product is filtered and ultrafiltered against PBS to remove all unreacted ligand.

Reaction Sequence 6

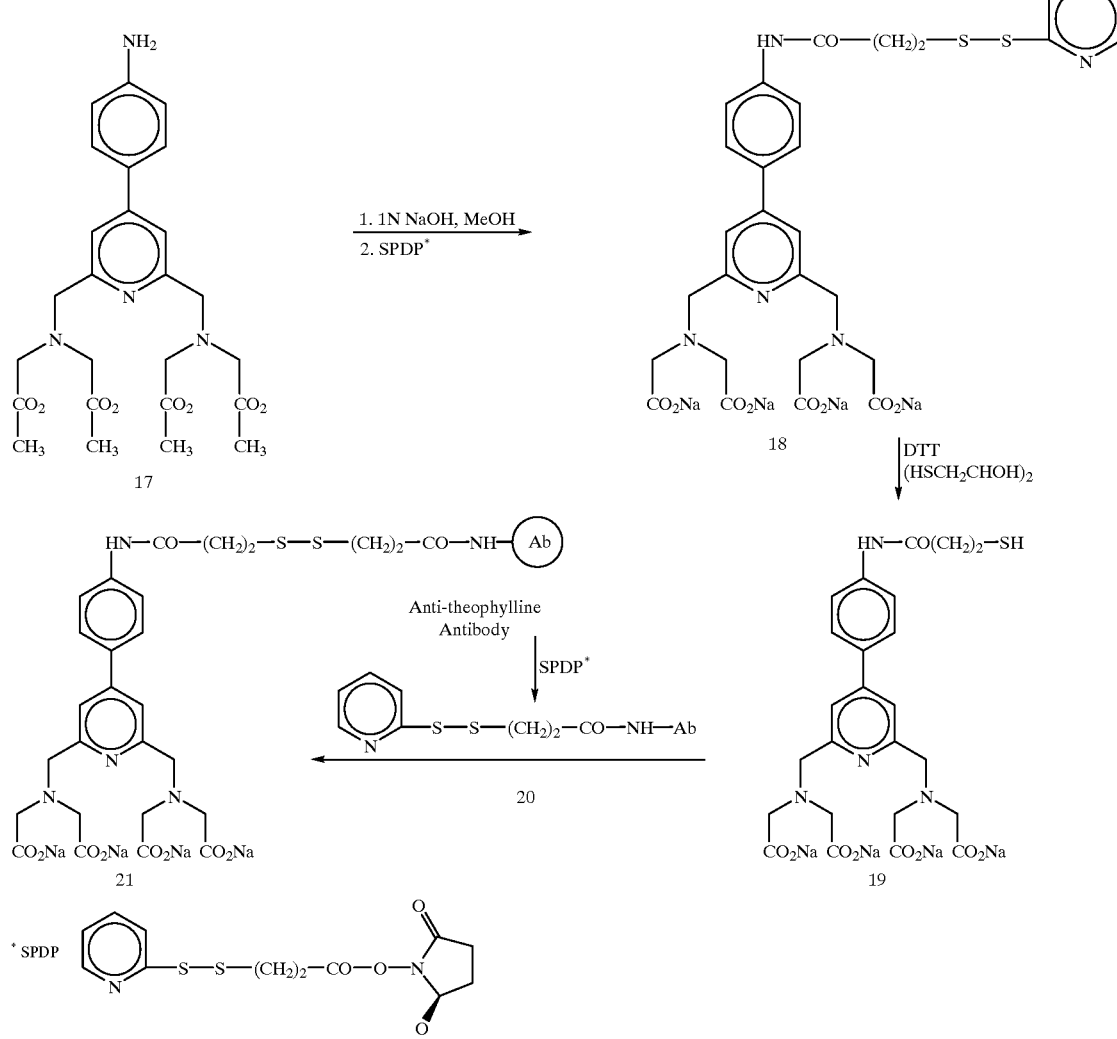

(10) This preparation follows Reaction Sequence 7. It begins with ligand 22 which is prepared from the 3-amino-tetraester of Part B of Example 4. One μmol of 22 in 57.4 μl of water is added to 36.8 μl (1 μmol) of DSS (Pierce Chemical) in DMSO. After 5 minutes at room temperature, 100 nmols of the resulting cloudy suspension of 23 is added to 10 nmols of affinity chromatography-purified anti-theophylline antibody. This mixture is held at room temperature for 15 minutes and then quenched with an equal volume (38.6 µl) of 1M ammonium acetate to yield leashed antibody 24 which is recovered by ultrafiltration. This antibody coupling is then repeated using the remaining 900 nmols of 23 and 9 nmols of antibody (ligand:antibody ratio of 100:1).

(11) This preparation follows Reaction Sequence 8. It is substantially a repeat of Example 10 above with the change that it begins with ligand 25 which is prepared from the 3-amino-tetraester of Part B of Example 4 and that it uses Pierce Chemical DST as coupling agent. A 100:1 molar ratio of ligand to antibody is employed to yield labeled anti-theophylline antibody 26.

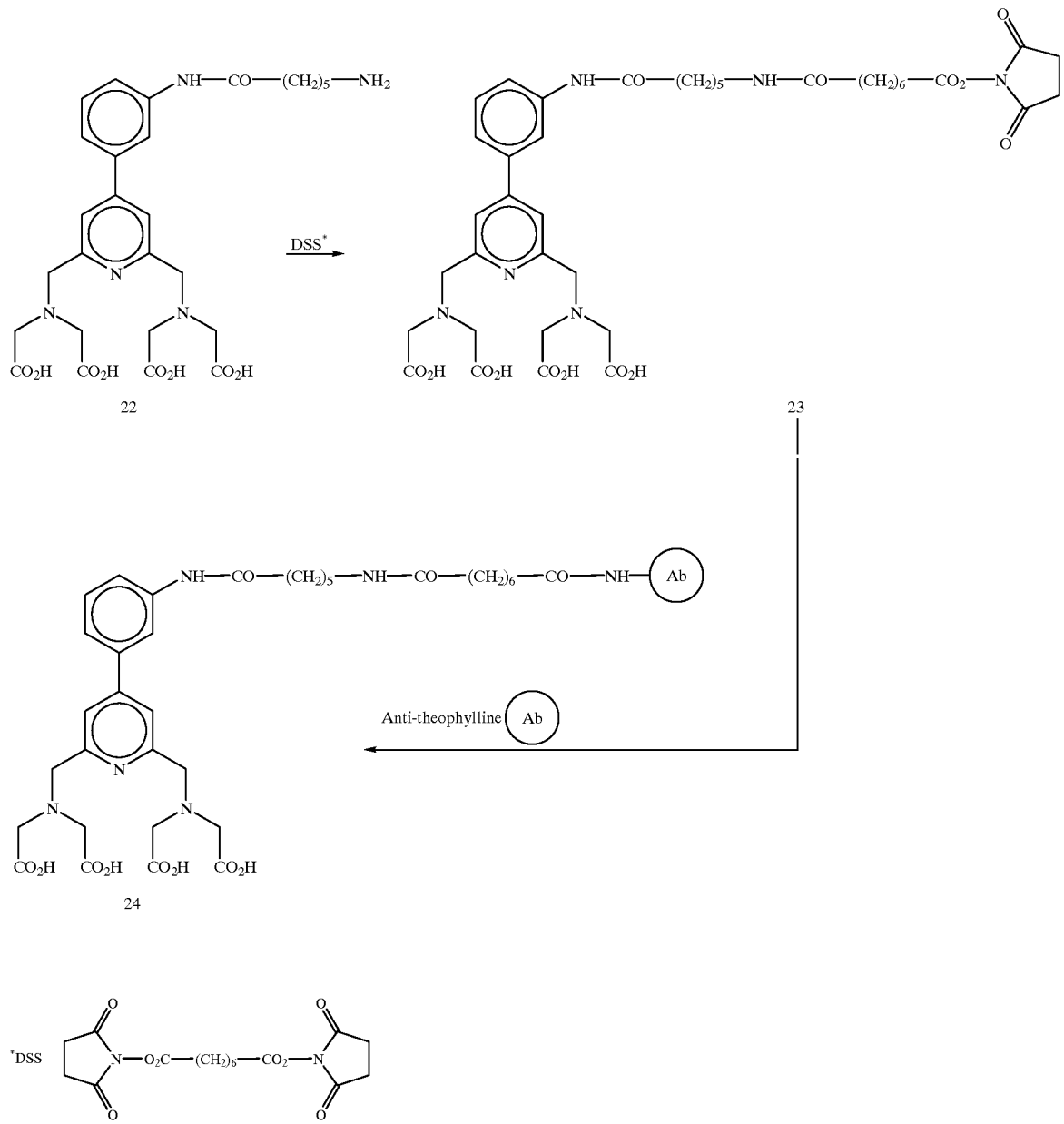

Reaction Sequence 8

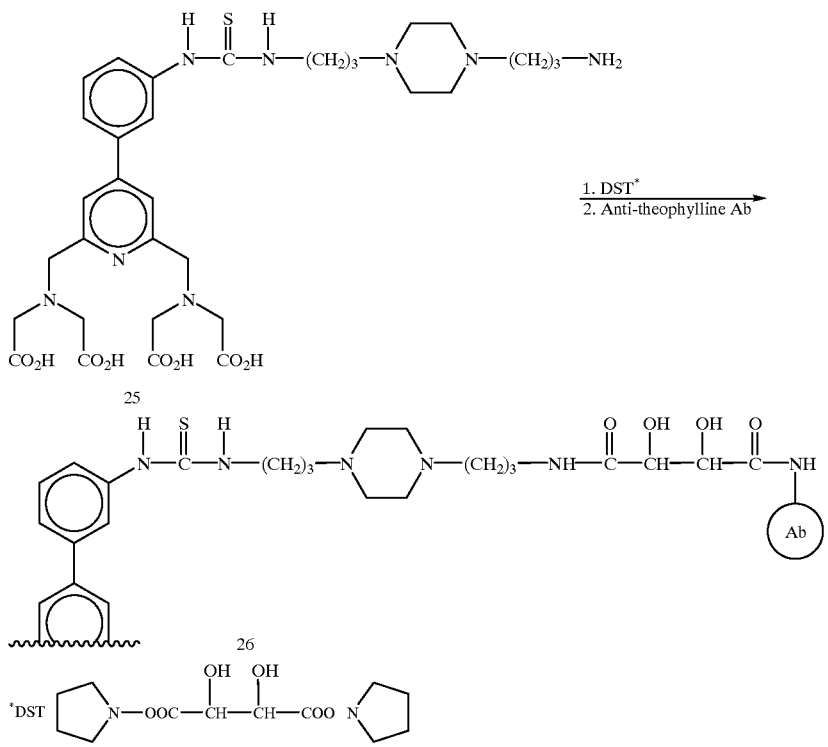

(12) As shown in Reaction Sequence 9, Example 11 above is repeated using Pierce Chemical DSS as coupling agent to yield labeled anti-theophylline antibody 27.

Reaction Sequence 9

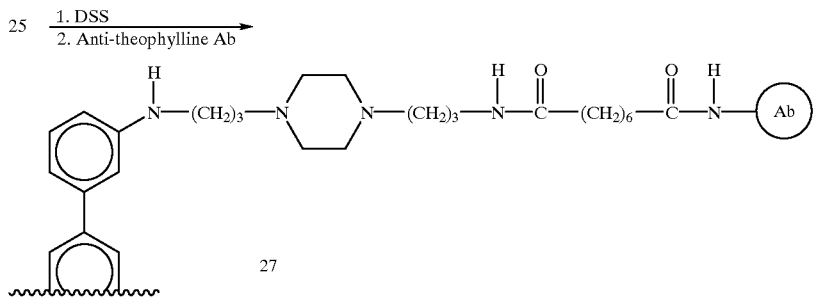

Examples 9 through 12 illustrate that ligands can be attached to antibodies through a wide range of lengths of linking groups so as to achieve proper control of ligand to ligand distances and facillitate metal transfer between such ligands.

EXAMPLE 13

A Fluorescence Enhancement Metal Transfer Assay

Terbium chelates of the theophylline-linked tri- and tetraacids of Examples 7 and 8 are prepared as follows. The tri- and tetraacids of these Examples are separately dissolved in 0.01M sodium borate solution to a concentration of $10^{-5}$M. Then an equivalent molar amount of aqueous terbium chloride is added to each and the mixtures are allowed to stand for a few minutes. Fluorescence measurements are carried out and demonstrate that 1:1 molar chelate complexes of the tetraacids and the terbium have been formed and that such complexes are stable but only modestly fluorescent.

An assay for theophylline is carried out by allowing one of the terbium chelate-labeled theophyllines to compete with theophylline standards for binding to one of the second ligand-linked anti-theophylline antibodies of Examples 9–12. The labeled theophylline on binding to antibody brings its terbium ion into close proximity of the second ligand attached to the antibody. The terbium ion is directly transferred to this second ligand thus forming a new chelate complex with the second ligand which is highly fluorescent and easily detectable using fluorescence-background rejection methods. The formation of this new chelate brings about an enhancement of its fluorescence and this enhancement is proportional to the amount of labeled theophylline bound and inversely proportional to the amount of theophylline present in the sample. The assay is carried out in polystyrene tubes (12×15 mm) to which 1 ml of pH 8.5 0.01M sodium borate buffer was added. This is followed by the addition of 10 μl of 1 μM tracer (8.7 ng) and 10 μl of theophylline standard (0, 5.4, 16.2, 54, and 540 ng). Addition of 25 μl of an about 0.3 μM solution of the second chelate-labeled anti-theophylline antibody in 0.01M borate containing 0.1M sodium chloride and 1% normal human serum (final concentration in assay tube about 7.5 μnM) leads to increases in the observed fluorescence which are inversely proportional to the levels of theophylline in the samples.

EXAMPLE 14

A Mixed Ligand Assay

This Example demonstrates the application of the principles of a mixed ligand homogeneous assay in which the target-like molecule is a relatively nonfluorescent chelate of terbium and the antibody-like molecule is an anti-target antibody to which has been conjugated a suitable second ligand comprising a fluorophore group as well as a chelating group. Specifically, following the process of Example I.C of U.S. patent application Ser. No. 712,774, the phenylpyridine diacid 28 was prepared. As shown in Reaction Sequence 10, nitration followed by reduction of the nitro group to an amine and conjugation to antitheophylline antibody using disuccinimidyl suberate gave 29 as the antibody-like member of the specific-binding pair. The theophylline-linked tri- and tetraacid chelates whose preparation is described in Examples 7 and 8 function as the target-like members of the specific-binding pair. Upon formation of the bound complex, the pyridine diacid functionality of the fluorophore ligand on the antibody is sufficiently close and is capable of occupying coordination sites of terbium not occupied by the tri- or tetraacids of the targetlike theophylline derivative. If analyte theophylline reacts with the antibody it does not bring with it a complex-forming diacid. The phenylpyridine fluorophore of the mixed ligand enhances the fluorescence of the chelate and the extent of such enhancement is inversely proportional to the amount of analyte theophylline in the sample being assayed.

Reaction Sequence 10

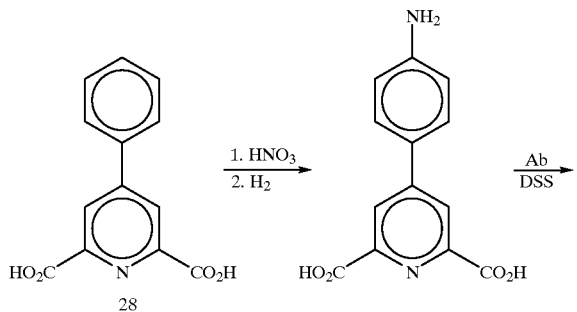

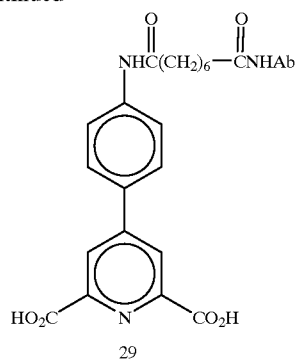

What is claimed is:

1. In a homogeneous fluorescent-based detection system, the method comprising the steps of carrying out a biospecific binding reaction between a biospecific group-containing compound and a binding partner, wherein at least one of the biospecific group containing compound and the binding partner are labeled with a fluorescent tag, then exciting the solution with electromagnetic radiation and thereafter detecting the fluorescent emission from the excited solution and relating that fluorescent emission to the extent of the biospecific binding reaction, the improvement comprising:

a. admixing a water-soluble first tag-containing biospecific group-containing compound with an aqueous solution, said aqueous solution containing a biospecific counterpart of said biospecific group-containing compound group, thereby forming an aqueous solution product containing a specific binding pair, which as a result of such specific binding, contains a new tag which is different in fluorescence from the first tag, at least one of the first tag and the new tag comprising a fluorescent chelate containing a rare earth metal, the chelate being water-soluble in said aqueous solution product, and having a metal to ligand binding constant greater than about $10^{13}M^{-1}$ and a decay lifetime that is longer than the longest decay lifetime of ambient substances;

b. exciting the aqueous solution product of step a. with at least one pulse of electromagnetic radiation, said pulse having a duration which is shorter than the decay lifetime of the long-lived fluorescent emission, thereby forming an excited solution product;

c. detecting the fluorescent emission from the excited aqueous solution product after the fluorescence of said ambient substances has substantially decayed; and d. relating the fluorescence detected in c. to the extent of specific binding reaction occurring in the aqueous solution.

2. The method of claim 1, wherein each of the first tag and the new tag are rare earth metal chelate complexes, the second of which has a quenched fluorescence as a result of the specific binding reaction.

3. The method of claim 1, wherein each of the first tag and new tag are rare earth metal chelate complexes, the second of which has an enhanced fluorescence as a result of the specific binding reaction.

4. The method of claim 2, wherein the quenched fluorescence is a result of energy transfer from the first tag to a group brought into proximity with the first tag by means of the specific binding reaction.

5. The method of claim 4, wherein the proximity is a distance of from about 5 Å to about 75Å.

6. The method of claim 5, wherein the rare earth metal chelate comprises terbium or europium.

7. The method of claim 6, wherein the group brought into proximity with the first tag by means of the specific binding reaction is the group which undergoes the specific binding reaction.

8. The method of claim 7, wherein the group brought into proximity is anti-theophylline antibody.

9. The method of claim 8, wherein the first tag is a europium chelate of an aryl-substituted 2,6-[N,N-bis (carboxylalkyl)aminoalkyl]pyridine ligand.

10. The method of claim 7, wherein the first tag is a terbium chelate of an aryl-substituted 2,6-[N,N-bis (carboxylalkyl)aminoalkyl]pyridine ligand.

11. The method of claim 6, wherein the group brought into proximity with the first tag by means of the specific binding reaction is a group attached to the group which undergoes the specific binding reaction.

12. The method of claim 11, wherein the energy is transferred to the ligand comprising the first tag.

13. The method of claim 11, wherein the group brought into proximity is a period IV transition metal complex.

14. The method of claim 11, wherein the group brought into proximity is a rhodamine.

15. The method of claim 3, wherein the enhanced fluorescence is a result of energy transfer to the first tag from a group brought into proximity with the first tag by means of the specific binding reaction.

16. The method of claim 1, wherein the first chelate complex has a stability at least about one order of magnitude less than the stability of the new chelate complex.

17. The method of claim 16, wherein the first tag is a europium or terbium chelate of an alkylpolyaminepolycarboxylic acid, and the new tag comprises a europium or terbium chelate of an aryl-substituted 2,6-[N,N-bis (carboxylalkyl)aminoalkyl]pyridine ligand.

18. The method of claim 16, wherein the new tag comprises a europium or terbium chelate of a 2,6-[N,N-bis (carboxylalkyl)aminoalkyl]phenanthroline ligand.

19. A homogeneous method for the quantitative determination of an analyte in a sample utilizing a fluorescent-based detection system, the method comprising the steps of carrying out a biospecific binding reaction between the analyte and a binding partner or between the analyte or an analyte analogue and a binding partner, wherein at least one of the analyte analogue and the binding partner are labeled with a fluorescent tag, then exciting the solution with electromagnetic radiation and thereafter detecting the fluorescent emission from the excited solution and relating that fluorescent emission to the extent of the biospecific binding reaction, the method further comprising:

a. admixing a water-soluble first tag-containing biospecific group-containing compound with an aqueous solution, said aqueous solution containing a biospecific counterpart of said biospecific group-containing compound group, thereby forming an aqueous solution product containing a specific binding pair which as a result of such specific binding contains a new tag which is different in fluorescence from the first tag, wherein each of the first and new tags are rare earth metal chelate complexes;

b. exciting the aqueous solution product of step a. with at least one pulse of electromagnetic radiation said pulse having a duration which is shorter than the decay lifetime of the long-lived fluorescent emission, thereby forming an excited aqueous solution product;

c. detecting the fluorescent emission from the excited aqueous solution product after the fluorescence of said ambient substances has substantially decayed; and d. relating the fluorescence detected in c. to the extent of specific binding reaction occurring in the aqueous solution.

20. A homogeneous method for the quantitative determination of a specific binding reaction in an aqueous solution which comprises:

a. admixing a water-soluble first tag-containing biospecific group-containing compound with biospecific counterpart thereby forming a specific binding pair which as a result of such specific binding contains a new tag which is different in fluorescence from the first tag, at least one of the first tag and the new tag comprising a fluorescent chelate containing a rare earth metal, the chelate being water-soluble and having a metal to ligand binding constant greater than about $10^{13} M^{-1}$ and a decay lifetime that is long compared to the longest decay lifetime of ambient substances;

b. exciting the aqueous liquid product of step a. with at least one pulse of electromagnetic radiation said pulse having a duration which is short compared to the decay lifetime of the long-lived fluorescent emission;

c. detecting the fluorescent emission from the sample after the fluorescence of said ambient substances has substantially decayed;

d. and relating the fluorescence detected in c. to the extent of specific binding reaction occurring in the solution.

* * * * *